(12) United States Patent
Lafontaine

(10) Patent No.: US 8,845,707 B2
(45) Date of Patent: Sep. 30, 2014

(54) CRYOTREATMENT DEVICE AND METHOD

(71) Applicant: Boston Scientific SCIMED, Inc., Maple Grove, MN (US)

(72) Inventor: Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/852,801

(22) Filed: Mar. 28, 2013

(65) Prior Publication Data

US 2013/0238064 A1    Sep. 12, 2013

Related U.S. Application Data

(60) Continuation of application No. 13/195,717, filed on Aug. 1, 2011, now Pat. No. 8,409,266, which is a continuation of application No. 11/734,762, filed on Apr. 12, 2007, now Pat. No. 8,012,147, which is a division of application No. 09/625,163, filed on Jul. 25, 2000, now Pat. No. 7,220,257.

(51) Int. Cl.
| | | |
|---|---|---|
| *A61F 7/00* | (2006.01) | |
| *A61B 18/02* | (2006.01) | |
| *A61F 7/12* | (2006.01) | |
| *A61B 19/00* | (2006.01) | |
| *A61B 17/22* | (2006.01) | |
| *A61B 17/00* | (2006.01) | |
| *A61B 18/00* | (2006.01) | |
| *A61B 18/18* | (2006.01) | |

(52) U.S. Cl.
CPC .................. *A61F 7/123* (2013.01); *A61B 18/02* (2013.01); *A61B 2019/4063* (2013.01); *A61B 2017/22051* (2013.01); *A61B 2017/22002* (2013.01); *A61B 2017/00867* (2013.01); *A61B 2018/00196* (2013.01); *A61B 2018/1861* (2013.01); *A61B 2018/0275* (2013.01); *A61B 2018/0287* (2013.01); *A61B 2018/0212* (2013.01); *A61B 2019/5278* (2013.01); *A61B 2017/00243* (2013.01); *A61B 2017/22067* (2013.01); *A61B 2018/0022* (2013.01); *A61B 2018/00041* (2013.01); *A61B 2019/464* (2013.01)
USPC .............................. 607/105; 607/96; 607/104

(58) Field of Classification Search
USPC ......... 607/96, 104–107; 606/7, 13–16, 20–31
See application file for complete search history.

(56) References Cited

U.S. PATENT DOCUMENTS

| | | |
|---|---|---|
| 3,125,096 A | 3/1964 | Antiles et al. |
| 3,712,306 A | 1/1973 | Bryne |

(Continued)

FOREIGN PATENT DOCUMENTS

| | | |
|---|---|---|
| GB | 1019028 A | 2/1966 |
| GB | 2283678 A | 5/1995 |

(Continued)

OTHER PUBLICATIONS

"Argon Beam Coagulation Compared with Cryoablation of Ventricular Subendocardium," Ann. Thorac. Surg., 1993. 1 page.

(Continued)

*Primary Examiner* — Ahmed Farah
(74) *Attorney, Agent, or Firm* — Seager, Tufte & Wickhem, LLC

(57) ABSTRACT

Devices and methods for cooling vessel walls to inhibit restenosis in conjunction with medical procedures such as coronary artery angioplasty. One catheter device includes a distal tube region having coolant delivery holes radially and longitudinally distributed along the distal region. In some devices, holes spray coolant directly onto the vessel walls. In other embodiments, a balloon or envelope is interposed between the coolant and the vessel walls and the coolant returned out of the catheter through a coolant return lumen. Some direct spray devices include an occlusion device to restrict blood flow past the region being cooled. Pressure, temperature, and ultrasonic probes are included in some cooling catheters. Some cooling catheters are coiled perfusion catheters supporting longer cooling periods by allowing perfusing blood flow simultaneously with vessel wall cooling.

10 Claims, 5 Drawing Sheets

(56) References Cited

U.S. PATENT DOCUMENTS

| | | | |
|---|---|---|---|
| 4,211,233 A | 7/1980 | Lin | |
| 4,278,090 A | 7/1981 | Van Gerven | |
| 4,367,743 A | 1/1983 | Gregory | |
| 4,580,499 A | 4/1986 | Fauvel et al. | |
| 4,784,133 A | 11/1988 | Mackin | |
| 4,860,744 A | 8/1989 | Johnson et al. | |
| 5,019,042 A | 5/1991 | Sahota | |
| 5,078,713 A | 1/1992 | Varney | |
| 5,108,390 A | 4/1992 | Potocky et al. | |
| 5,139,496 A | 8/1992 | Hed | |
| 5,147,355 A | 9/1992 | Friedman et al. | |
| 5,190,540 A | 3/1993 | Lee | |
| 5,281,215 A | 1/1994 | Milder | |
| 5,334,181 A | 8/1994 | Rubinsky et al. | |
| 5,334,193 A | 8/1994 | Nardella | |
| 5,335,669 A | 8/1994 | Tihon et al. | |
| 5,342,301 A | 8/1994 | Saab et al. | |
| 5,348,554 A | 9/1994 | Imran et al. | |
| 5,417,689 A | 5/1995 | Fine et al. | |
| 5,423,807 A | 6/1995 | Milder | |
| 5,443,470 A | 8/1995 | Stern et al. | |
| 5,454,807 A | 10/1995 | Lennox et al. | |
| 5,501,681 A | 3/1996 | Neuwirth et al. | |
| 5,520,682 A | 5/1996 | Baust et al. | |
| 5,536,252 A | 7/1996 | Imran et al. | |
| 5,624,392 A | 4/1997 | Saab et al. | |
| 5,674,218 A | 10/1997 | Rubinsky et al. | |
| 5,807,391 A | 9/1998 | Wijkamp | |
| 5,868,735 A | 2/1999 | Lafontaine et al. | |
| 5,902,299 A | 5/1999 | Jayaraman et al. | |
| 5,910,104 A | 6/1999 | Dobak, III et al. | |
| 5,957,917 A | 9/1999 | Doiron et al. | |
| 5,968,059 A | 10/1999 | Ellis et al. | |
| 5,971,979 A | 10/1999 | Joye et al. | |
| 6,012,457 A | 1/2000 | Lesh | |
| 6,024,740 A | 2/2000 | Lesh et al. | |
| 6,106,518 A | 8/2000 | Wittenberger et al. | |
| 6,149,677 A | 11/2000 | Dobak et al. | |
| 6,179,835 B1 | 1/2001 | Panescu et al. | |
| 6,193,644 B1 | 2/2001 | Dobak, III et al. | |
| 6,264,679 B1 | 7/2001 | Keller et al. | |
| 6,283,959 B1 | 9/2001 | Lalonde et al. | |
| 6,290,696 B1 | 9/2001 | Lafontaine | |
| 6,348,067 B1 | 2/2002 | Baum et al. | |
| 6,355,029 B1* | 3/2002 | Joye et al. | 606/21 |
| 6,428,563 B1* | 8/2002 | Keller | 607/105 |
| 6,432,102 B2 | 8/2002 | Joye et al. | |
| 6,517,533 B1 | 2/2003 | Swaminathan | |
| 6,542,781 B1 | 4/2003 | Koblish et al. | |
| 6,673,066 B2 | 1/2004 | Werneth | |
| 6,904,303 B2* | 6/2005 | Phan et al. | 600/374 |
| 6,953,460 B2 | 10/2005 | Maguire et al. | |
| 7,220,257 B1 | 5/2007 | Lafontaine | |
| 7,291,144 B2 | 11/2007 | Dobak, III et al. | |
| 7,507,234 B2* | 3/2009 | Utley et al. | 606/21 |
| 8,012,147 B2 | 9/2011 | Lafontaine | |
| 8,409,266 B2 | 4/2013 | Lafontaine | |
| 2001/0037081 A1 | 11/2001 | Heiner | |
| 2002/0022832 A1 | 2/2002 | Mikus et al. | |
| 2002/0032438 A1 | 3/2002 | Lafontaine | |
| 2002/0045892 A1 | 4/2002 | Kramer | |
| 2002/0072738 A1* | 6/2002 | Edwards et al. | 606/41 |
| 2002/0091378 A1 | 7/2002 | Dobak, III et al. | |
| 2008/0300585 A1 | 12/2008 | Dobak, III et al. | |
| 2012/0143293 A1 | 6/2012 | Mauch et al. | |

FOREIGN PATENT DOCUMENTS

| | | |
|---|---|---|
| GB | 2336782 A | 11/1999 |
| GB | 2337000 B | 8/2000 |
| WO | 9712557 A1 | 4/1997 |
| WO | 9927862 A1 | 6/1999 |
| WO | 0047118 A1 | 8/2000 |
| WO | 0207625 A2 | 1/2002 |
| WO | 02083196 A2 | 10/2002 |

OTHER PUBLICATIONS

"Cardiac Rhythm Disturbances due to Caval Occlusion During Hepatic Cryosurgery," Cryobiology, 1994. 1 page.

"Cox Maze Operation Without Cryoablation for the Treatment of Chronic Atrial Fibrillation," Annals of Thoracic Surgery, 1995. 1page.

"Histologic Study of Chronic Catheter Cryoablation of Atrioventricular Conduction in Swine," Am. Heart. J., 1993. 1 page.

"Intractable Chest Pain in Cardiomyopathy: Treatment by a Novel Technique of Cardiac . . . ," Br. Heart J., 1993. 1 page.

"Percutaneous Serial Catherization in Swine: a Practical Approach," J. Invest. Surg., 1995. 1 page.

"Prostate Cryosurgery now Reimbursable in Southern California," Healthcare Technology Management. 1 page.

"Renal Cryoablation in a Canine Model," Urology, 1996. 1 page.

Cahan et al., "Five years of Cryosurgical Experience: Benign and Malignant Tumors with Hemorrhagic Conditions," Cryosurgery, 1968, Chapter 21, pp. 388-391.

Coger et al., "Preservation Techniques for Biomaterials," The Biomedical Engineering Handbook, 1995. 8 pages.

Fuller and Grout, "Cryopreservation of Other Tissues," Clinical Applications of Cryobiology, 1991, pp. 181 and 229-230.

Hunt et al., "Fractures in Cryopreserved Arteries," Cryobiology, 1994, 31:506-515.

Mazur, "Physical-Chemical Factors Underlying Cell Injury in Cryosurgical Freezing," Cryosurgery, 1968, Chapter 3, pp. 32-51.

McGrath, "Mechanical Properties of Membranes," Effects of Low Temperatures on Biological Membranes, 1981, pp. 346-347.

Nataf et al., "Effect of Cold Anoxia and Cryopreservation on Metabolic and Contractile Functions of Human Mammary Artery," Cryobiology, 1995, 32:327-333.

Schilling et al., "Nature of the Vehicle for Cryopreservation of Human Peripheral Veins: Preservation of Reactivity to Pharmacological Stimuli," Cryobiology, 1995, 32:109-113.

Zacarian, "The Effects of Sub-Zero Temperatures on the Microvessels," Cryosurgery of Tumors of the Skin and Oral Cavity, 1973, Chapter 3, pp. 38-39 and 48-53.

Morris et al., "Effects of Low Termperatures on Biological Membranes," 2 pages, published on or prior to Jan. 12, 1999.

* cited by examiner

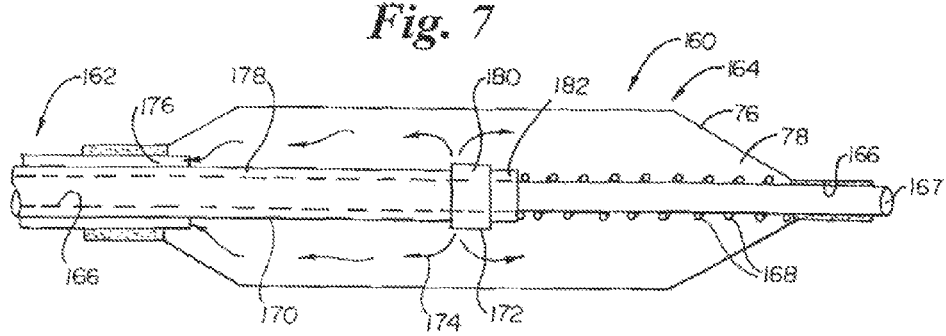
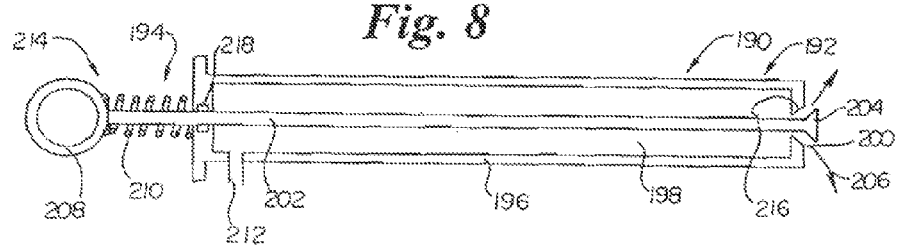
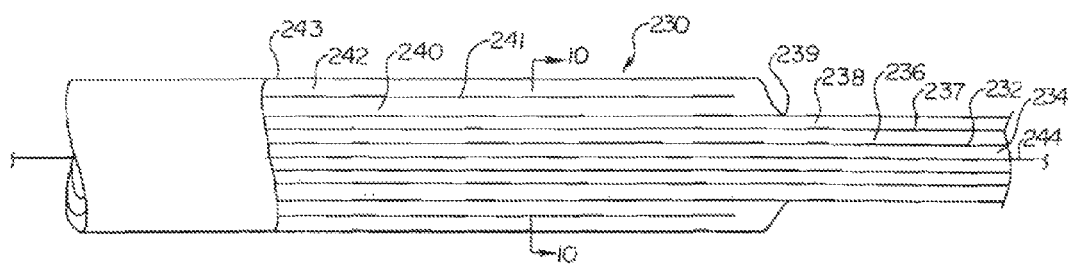
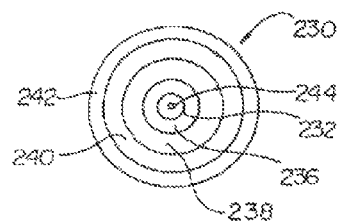

CRYOTREATMENT DEVICE AND METHOD

CROSS REFERENCE TO RELATED APPLICATIONS

The present application is a continuation of a U.S. application Ser. No. 13/195,717, filed Aug. 1, 2011, now U.S. Pat. No. 8,409,266; which is a continuation of U.S. application Ser. No. 11/734,762, filed Apr. 12, 2007, now U.S. Pat. No. 8,012,147; which is a divisional of and claims the benefit under 35 U.S.C. §121 of U.S. patent application Ser. No. 09/625,163, filed Jul. 25, 2000, now U.S. Pat. No. 7,220,257; which is related to U.S. patent application Ser. No. 09/229,080, filed Jan. 12, 1999, now U.S. Pat. No. 6,290,696; which is a divisional of U.S. patent application Ser. No. 08/812,804, filed Mar. 6, 1997, now U.S. Pat. No. 5,868,735; the entire disclosures of which are all incorporated herein by reference.

FIELD OF THE INVENTION

The present invention is related generally to medical devices and methods. More specifically, the present invention relates to devices and methods for cooling internal body locations. The present invention includes methods for cooling stenosed blood vessel regions prior to and subsequent lo angioplasty to inhibit restenosis.

BACKGROUND OF THE INVENTION

Conventional angioplasty has been performed for several decades, prolonging the lives of an ever-increasing number of patients. Angioplasty procedures involve the dilatation of a balloon placed across a lesion in a coronary artery. Dilatation of the balloon in turn dilates the lesion, opening the artery for increased blood flow. In some cases, however, the goal of the angioplasty procedure is, in whole or in part, frustrated by complete or partial reclosure of the artery at the lesion. Two mechanisms are believed to be principally responsible for reclosure of the artery, these are restenosis and recoil. Restenosis is believed to be caused by continued growth or regrowth of the smooth muscle cells associated with the lesion. Recoil is in part a mechanical process involving elastic rebound of the dilated lesion.

Several means have been disclosed for addressing the problem of restenosis. These include, among others, radiation treatments to slow or prevent smooth muscle cell proliferation associated with the restenotic process. Certain drug therapies have been proposed to prevent or slow restenosis.

Several means have also been developed to address the issue of recoil. One of the more significant developments in this area has been stents, which can be permanently deployed to mechanically hold open lesions. Although stents have been found to be highly effective, they may irritate the wall of a artery in which they are implanted. Some believe that this may encourage limited restenosis. Warming of the lesion during dilatation has also been disclosed to prevent or slow recoil. Warming the lesion is believed to soften the lesions such that it may be "remodeled" that is, thinned under low pressure. Heating of the lesion, however, is believed to cause an injury response which may cause some restenosis.

What would be desirable and advantageous is a method and apparatus for reducing the likelihood of restenosis.

SUMMARY OF THE INVENTION

The present invention includes devices and methods for reducing adverse reactions to medical procedures impacting body vessels such as blood vessels by cooling the effected vessel regions. The invention includes methods and devices for cooling blood vessel sites having a lesion which arc to be impacted by angioplasty. The vessel wall cooling can be performed before, during, and/or after the angioplasty procedure and any combinations thereof. The cooling is believed to lessen any injury response which may be caused by the angioplasty, as the body may interpret the angioplasty procedure as an injury and react in ways that can cause restenosis.

One set of methods according to the present invention include distally advancing a tubular catheter having numerous radially outwardly pointing coolant distributing orifices supplied by a coolant lumen in fluid communication with a proximal coolant source. The coolant can be sprayed in the direction of the vessel wall and toward the lesion. One device used includes an expandable occlusion device for expanding against the vessel walls and greatly reducing, if not stopping, blood flow during the procedure. Occluding the blood vessel can reduce the vessel wall warming which is caused by blood flow through the vessel. Occluding the vessel also lessens the removal of coolant by the flowing blood. Occluding devices can be disposed on the cooling catheter shaft proximally and/or distally of the coolant distributing orifices. Inflatable occluding devices can be inflated by either the coolant fluid or by an inflation fluid other than the coolant. The coolant can be liquid, gas, or liquid that changes phase to gas during the cooling process.

One device for cooling a length of body vessel interior includes means for distributing coolant at multiple locations over the vessel interior. The device can also have a coolant delivery shaft having a first lumen coupled to tire coolant distribution means. Some devices also have means for occluding the body vessel interior, for example, an inflatable occluding element. One embodiment uses the coolant as an inflation fluid. Some embodiments include a second lumen for inflating the occluding element. One group of embodiments utilize an inflatable balloon or skirt. In general, the cooling catheter can include a distal region for radially and longitudinally distributing coolant simultaneously over the target vessel region. The infused coolant can be absorbed into the blood and carried downstream. In some methods, the cooling catheter distal region includes pressure and/or temperature sensors coupled to external readouts for following the progress of the procedure. One method utilizes an ultrasonic transducer disposed in the catheter distal region for determining freeze status of the lesion or vessel walls. In one method, an ultrasonic transmitter is disposed within the vessel which can be monitored by a receiver outside the body. In another embodiment, an ultrasonic receiver is disposed within the vessel, which receives externally generated ultrasound. The attenuation of sound by the vessel walls and any lesion is less for frozen tissue than for unfrozen tissue. In one method, the internal pressure of the vessel is measured and followed to maintain the pressure in the vessel within specified limits.

One device used according to the present invention includes an envelope or inflatable balloon disposed between the coolant distributor and the blood vessel wall. In this embodiment, the coolant does not contact the lesion directly but cools the lesion through the balloon envelope wall. One embodiment of this device can radially and longitudinally distribute coolant over the length of vessel inside the balloon with a rotatable and axially slidable coolant distributing probe which can have a distal bend or curve with a distal most delivery orifice. The slidable and rotatable coolant delivery tube can be aimed at different locations at different times to cover whatever target sites are desired. Using this embodiment, one side of the vessel wall can be targeted for cooling whille an opposing or adjacent site left uncooled or less cooled. The catheter can include pressure and temperature sensors inside the balloon as well as an ultrasonic transducer. Some embodiments include guide wire tubes through the balloon while other embodiments have fixed wires extending through the balloon. Some embodiments utilize a liquid coolant while others utilize a coolant which vaporizes from liquid to gas inside the balloon.

Coolant can exit the balloon interior through an exhaust or return opening extending from the balloon interior. In some embodiments, the exhaust port exits from the balloon interior and into the blood stream. In other embodiments, the return port leads to a return lumen extending proximally through the catheter shaft. Some embodiments have a pressure control valve in fluid communication with the balloon interior to maintain the balloon pressure above a minimum, below a maximum, or both. In some embodiments, a pressure control valve is disposed near the proximal end of the catheter shaft in communication with a coolant return lumen. A pressure control valve can be used in conjunction with liquid carbon dioxide as a coolant to maintain the pressure inside the balloon above the triple point of carbon dioxide to inhibit dry ice formation when the liquid carbon dioxide vaporizes.

Catheters according to the present invention can include a longitudinally and radially spraying coolant distributor having multiple distributor tubes feed off a common manifold. In one embodiment, the multiple tubes have varying lengths and have outwardly directed spray orifices disposed near the tube ends. The multiple tubes can thus cover various angular sectors and can cover the length of the distributor LO include a vessel interior region. Some embodiments are used directly within a vessel interior while other embodiments are used within a balloon or envelope interposed between the distributor and the vessel walls. Another coolant distributor embodiment includes a longitudinally disposed tube having numerous holes through the tube wall into a coolant lumen within. In one embodiment, the holes are visible with the unaided eye while another embodiment has micropores not individually viewable with the unaided eye.

One cooling balloon catheter includes a pressure-regulating valve disposed between a coolant supply tube and the balloon interior. When the coolant supply tube pressure exceeds a pressure level, the valve can open and release coolant into the balloon interior, in one embodiment, the valve includes a cap covering the coolant tube distal end which is biased shut by a spring. In one catheter, the valve is slidingly disposed over a guide wire tube. One coolant-distributing device includes an elongate tube having a coolant lumen and a control rod or control wire therethrough. The control rod or wire can be operably connected to a distal spring-loaded valve, with the spring disposed wherever practicable on the device. The distal valve can be opened away from a valve seat allowing coolant to escape from the tube. In some embodiments, the distal valve is shaped to spray radially outward toward the vessel interior walls.

Catheters incorporating the present invention can include warming jackets to lessen unwanted cooling by catheter regions proximal of the distal cooling region. The warming jacket can include a substantially annular warming fluid supply lumen as well as an optional warming fluid return lumen. In some embodiments, saline is used as the warming fluid and is vented out the catheter distal end into the blood stream. The warming fluid can reduce the cooling caused by the coolant lumen or lumens disposed in the catheter shaft.

Perfusion cooling catheters are also within the scope of the present invention. Perfusion cooling catheters can provide for prolonged cooling of the vessel walls by including a perfusion pathway to allow blood flow past or through the distal cooling end of the catheter. One embodiment includes a helical coil supplied with coolant through a coolant lumen disposed in a longitudinal shaft. Perfusing blood flow is allowed through the lumen passing through the coil center. Another embodiment includes a radially expandable helical coil. One expandable helical coil is biased to assume a coiled configuration when unconstrained. The coiled can be substantially straightened by a stiffening member or wire inserted through the coil. The relatively straightened coil can be inserted through the vasculature to the site to be cooled. Once at the site, the stiffening wire can be retracted, allowing the unconstrained coil portion to assume the coil shape. One embodiment includes only a single turn coil while other embodiments include multiple turn coils. One perfusion catheter has a pressure reducing orifice near the cooling region inlet to provide cooling through a pressure drop. This catheter can be used in conjunction with a vaporizing coolant such as liquid carbon dioxide to provide a cold distal cooling region. One embodiment includes a fluid block near the coil outlet which can serve to block the return of liquid coolant in a liquid to gas, vaporizing cooling coil.

One cooling catheter is a catheter selected to be undersized relative to the vessel region to be cooled. The undersized catheter can cool the vessel walls without directly contacting the walls with the cooling balloon. The cooling balloon can include cooling balloons previously discussed, and having an outside diameter less than the inside diameter of the vessel region to be cooled. One end of the balloon, such as the proximal end, can include a radially expandable skirt which can serve to both occlude blood flow and to center one end of the balloon. The skirt can stop or greatly reduce blood flow between the balloon outer walls and the vessel inner walls. The quiescent volume of blood can be cooled by the balloon, with the blood volume in turn cooling the vessel walls. This design allows vessel wall cooling without substantial direct contact by a cold balloon wall. It may be desirable in some applications to minimize direct contact between an extremely cold balloon and a vessel wall. Some embodiments include both a proximal and a distal expandable skirt, which can provide improved centering and better isolation of a blood volume to be cooled. Some embodiments utilize skirts inflated by the coolant and having an inflatable outer ring. Some embodiment expandable skirts are expanded using an inflation fluid different than the coolant.

In use, the present invention can be used to cool a stenosed vessel region that is about to be dilated with angioplasty, is being dilated, or already has been dilated. The cooling preferably does not freeze the vessel cell walls sufficient to cause substantial cell death.

In use, the present invention can also be used to freeze tissue, causing tissue necrosis, for example, to treat arrhythmias. Tissue sites include tissue of the heart chamber walls and a suitably targeted interior wall of a pulmonary vein. In some such applications coolant is directly sprayed onto the tissue to be cryoablated. The direct spray can be directed in many directions about the coolant delivery tube or directed primarily in one direction. In other applications coolant is sprayed toward the tissue to be frozen, with a balloon envelope interposed between the coolant and the tissue. Cryoablation can be accomplished with perfusion cooling balloons and with cooling devices having inflatable occlusion balloons or skirls.

BRIEF DESCRIPTION OF THE DRAWINGS

FIG. 7 is a fragmentary, longitudinal, cross-sectional view of a cooling catheter having a spring-loaded pressure relief valve coolant distributor;

FIG. 8 is a longitudinal, cross-sectional view of a coolant delivery catheter having a proximal spring loaded control handle coupled to a distal valve;

FIG. 9 is a fragmentary, cross-sectional view of a cooling catheter shaft region having a warming jacket;

FIG. 10 is a transverse cross-sectional view taken along plane 10-10 of FIG. 9;

DETAILED DESCRIPTION OF THE INVENTION

Figure 1:
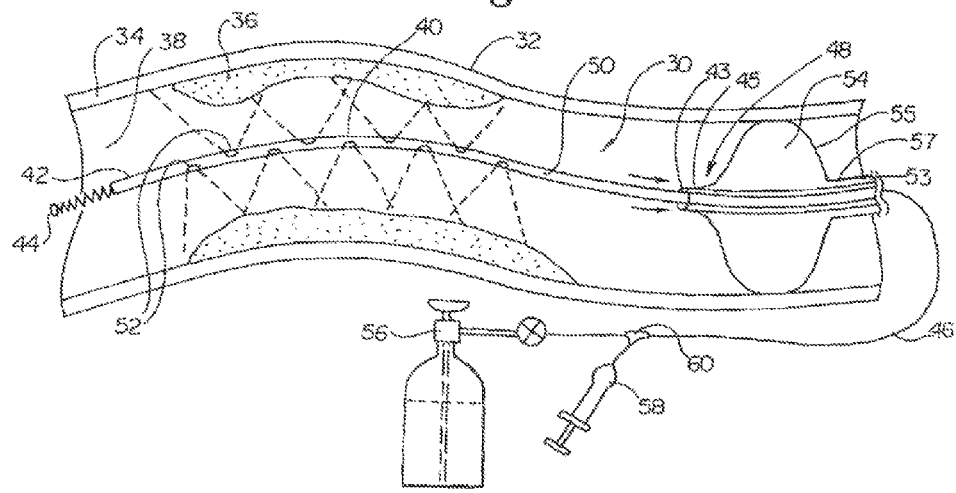
FIG. 1 is a fragmentary, longitudinal cross-sectional view of a stenosed vessel region having a catheter occluding the vessel and distributing coolant onto or near the stenosis.

FIG. 1 illustrates a vessel cooling device 30 disposed within a body blood vessel 32 having a vessel wall 34, a lumen 38 therethrough, and a stenosis, lesion, or plaque 36 partially occluding the vessel lumen and extending over a length of vessel. In the embodiment illustrated, cooling device 3$u$ includes a tubular shaft 48 having a proximal region 46, distal region 40, a distal end 42, and a distal tip 44. Shaft 48 includes a coolant tube 50 having a lumen therethrough and a plurality of coolant delivery orifices 52 disposed longitudinally and radially about the shaft distal region. The coolant is illustrated as spraying directly on the lesion. Cooling device 30 also includes an occlusion device 55 for occluding the vessel lumen. In the embodiment illustrated, an annular exhaust lumen 43 is defined between coolant tube 50 and a coaxially disposed exhaust tube 45. Exhaust tube 45 can be used to remove coolant from the vessel, in either liquid or gaseous form. In this embodiment, an annular inflation lumen 53 for expanding occlusion device 55 is defined between exhaust tube 45 and a coaxially disposed inflation tube 57. Cooling device 30 is illustrated having proximal region 46 extending out of the body to a coolant supply 56, and an inflation fluid supply 58. In the embodiment illustrated in FIG. 1, occlusion device 55 includes an inflatable balloon having a balloon interior 54. In the embodiment illustrated, balloon 55 is inflated with an inflation fluid different than the coolant fluid. In other embodiments, the occlusion device is inflated or expanded using the coolant fluid itself. In some embodiments, the coolant is supplied as a liquid which vaporizes into a gas and the gas inflates the occlusion device. Coolant supply 56 and inflation fluid supply 58 are illustrated joining to shaft proximal region 46 at a manifold 60.

Coolant supply 56 can provide a variety of coolants, depending on the embodiment of the invention elected. In some embodiments, a liquid coolant such as saline, nitrous oxide or ethyl alcohol is used. In other embodiments, a liquid coolant is used that can vaporize to a gas upon application. Liquid coolants that can vaporize to a gas and provide cooling include $CO_2$, nitrogen, liquid nitrous oxide, Freon, CFC's, HFC's, and other noble gasses In the embodiment illustrated in FIG. 1, the coolant is sprayed directly onto the stenosis. Orifices 52 distribute the coolant both longitudinally over a length of the shaft and radially about the shaft, using coolant distribution simultaneously through multiple orifices. Occlusion device 54, when used, can serve to enhance the cooling effect by blocking or greatly inhibiting blood flow which can warm the area to be cooled. In embodiments utilizing coolants which vaporize upon delivery, the vessel lumen may contain a moderate amount of gas, which can be absorbed by the body as long as the amount is maintained below a safe limit. In some methods, the gas can displace a large amount of blood, forcing some blood further downstream. In some embodiments, the catheter shaft includes a pressure sensor for measuring the internal pressure of the blood vessel for external readout.

In another use of cooling devices according to the present invention, cooling device 30 can be used to ablate or cause tissue necrosis through tissue freezing, for example within a chamber of the heart or within a pulmonary artery. Tissue may be ablated for various reasons, with the treatment of cardiac arrhythmias being a primary goal of one such treatment. In such applications, the cooling is continued for a time and temperature sufficient to cause cell death. In one such application, similar to the method illustrated in FIG. 1, the coolant is sprayed directly onto the tissue to be ablated. Cooling device 30 and subsequent cooling devices discussed are believed to be suitable for causing tissue necrosis as well as inhibiting restenosis through cooling. In one application, a circumferential region is ablated at a location where a pulmonary vein extends from a posterior left atrial wall of a left atrium in a patient. In one method, tissue is cooled to about 40 degrees Centigrade for a time period greater than about 3 minutes. Tissue ablation to treat arrhythmia is well known to those skilled in the art. See, for example, U.S. Pat. Nos. 5,147,355 and 6,024,740, herein incorporated by reference.

Figure 2:
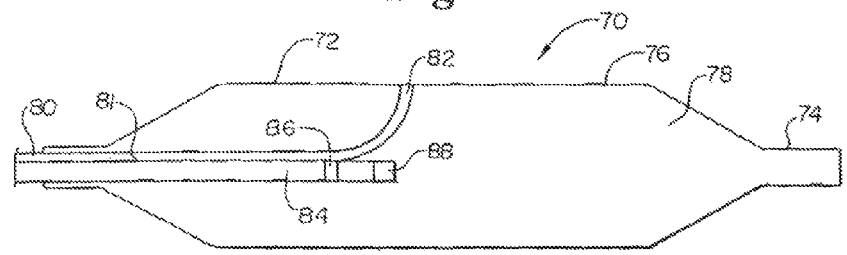
FIG. 2 is a fragmentary, longitudinal cross-sectional view of a catheter having an axially and radially moveable coolant distributing tube and instrument probe disposed within an inflatable balloon.

Referring now to FIG. 2, another cooling device 70 is illustrated, having a distal region 72 and a distal end 74. Cooling device 70 includes a longitudinally and radially moveable coolant directing tube 80 having a lumen 81 and terminating in a coolant orifice 82. A balloon envelope 76 is interposed between coolant orifice 82 and any vessel stenosis on the vessel interior walls. Balloon envelope 76 defines a balloon interior 78 in device 70. In some embodiments, an instrument probe 84 having a pressure sensor 86 and an ultrasonic transducer 88 is disposed within the balloon. On some embodiments the coolant and instrument shaft are independently moveable while in other embodiments, the two shafts move longitudinally and rotationally together. In some embodiments, the instrument devices are mounted on the same shaft used to deliver the coolant. One advantage of moving the coolant delivery tube and instruments together is the position of the coolant tube can be represented by the position of the instrument. Ultrasonic signals transmitted by ultrasonic transducer 88 can be picked up by external monitoring devices to determine the location of the probe, the extent of the stenosis, and, while cooling, the extent of the cooling, as the stenosis, if frozen, can show up distinctively on ultrasound images. Cooling device 70 utilizes longitudinal and rotational movement of coolant delivery orifice 82 to distribute coolant at the desired locations within the vessel interior. The balloon envelope separates the coolant from the vessel interior wall but allows cooling of the vessel interior by the directed coolant delivery, as the balloon envelope can readily transmit heat. Device 70 illustrates an over-the-wire balloon catheter having the guide wire removed. In some embodiments, the guide wire is removed from a shaft lumen which is then used to guide the coolant delivery tube to position inside the balloon. Some embodiments utilize the coolant to inflate the balloon while other embodiments utilize a separate inflation fluid. Some embodiments have the balloon interior pressure controlled by a pressure regulating valve allowing fluid out of the balloon interior only when the fluid has reached a sufficiently high pressure, In one embodiment, this valve is located near the balloon distal tip, allowing fluid exhaust into the blood stream. In another embodiment, this valve is disposed as the proximal end of an exhaust lumen extending through the catheter shaft.

Utilizing a rotationally and longitudinally moveable coolant delivery orifice allows the coolant to be delivered to spot locations along the vessel wall. In particular, lesions on only one side of the vessel can be isolated and cooled more than the opposing vessel wall. Cooling only the desired location can provide the desired degree of cooling in the location of the lesion without possibly overcooling vessel wall locations having no lesion present. In another use, device 70 can be used to cryoablate tissue in a pulmonary artery or within the heart.

Figure 3:
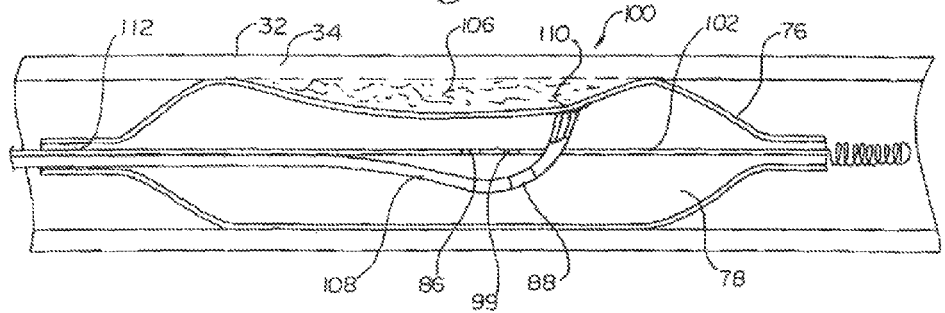
FIG. 3 is a fragmentary, longitudinal cross-sectional view of a fixed wire catheter having an axially and radially moveable coolant distributing tube and sensors disposed within an inflatable balloon disposed within a stenosed vessel.

Referring now to FIG. 3, a cooling device 100 is illustrated in a fixed wire embodiment, having balloon envelope 76, balloon interior 78, and a longitudinal stiffening wire 102 disposed through the balloon. Cooling device 100 includes pressure sensor 86 and a temperature sensor 99 disposed on wire 102. Ultrasonic device 88 is disposed on a distally bent or curved coolant delivery tube 108. Coolant delivery tube 108 terminates in a coolant delivery distal orifice 110, shown directed toward a stenosis 106 lying along one wall of vessel 32. As illustrated, balloon envelope 76 can lie against stenosis 106, largely precluding warming blood flow between the balloon and vessel wall. The embodiment illustrated in FIG. 3 also includes a coolant exhaust lumen 112, providing an exhaust route for coolant leaving the balloon. In some embodiments, the exhaust lumen includes a pressure-regulating valve to maintain the balloon interior pressure above a minimum. Cooling device 100 can also be used to cryoablate tissue in a pulmonary artery or within the heart, as previously discussed.

Figure 4:
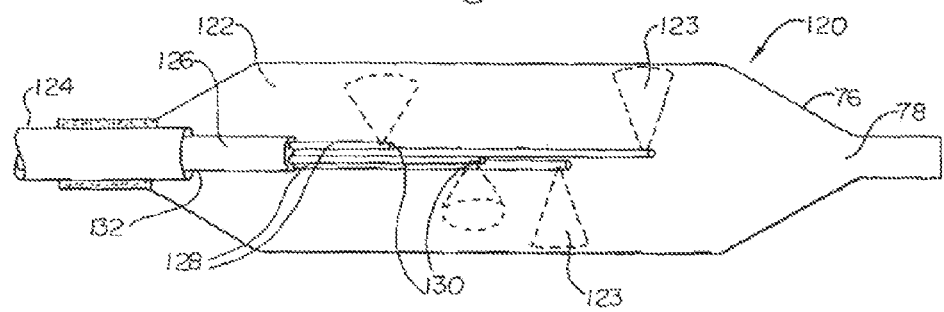
FIG. 4 is a fragmentary, cut-away, perspective view of a catheter having a coolant distributor including multiple distributor tubes of varying lengths disposed within a balloon.
Figure 5:
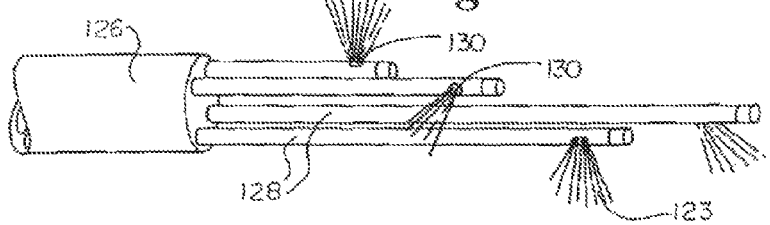
FIG. 5 is a fragmentary, perspective view of the coolant distributor of FIG. 4.

Referring now to FIG. 4, a cooling device 120 is illustrated, having a shaft 124 including a coolant supply tube 126 feeding a plurality of coolant distribution tubes 128 terminating near radially outwardly directed coolant delivery orifices or nozzles 130. Orifices 130 are illustrated establishing a spray pattern 123 against or in the direction of balloon envelope 76. Device 120 also includes an annular coolant return lumen 132 for allowing spent coolant to exit the balloon. FIG. 5 illustrates the coolant distributors in farther detail, showing coolant supply tube 126 feeding coolant distributor tubes 128 which feed orifices 130. As illustrated, cooling device 120 distributes coolant longitudinally over a length of balloon and also radially distributes coolant within the balloon interior. In some embodiments, coolant distributor tubes 128 have orifices 130 oriented toward the same radial direction, and this radial direction of vessel interior wall can be selected for cooling by rotating coolant supply tube 126. Coolant distribution tubes 128 can be formed of suitable materials including, for example, Nitinol. Cryoablation of tissue in a pulmonary artery or within the heart is also possible using cooling device 120.

Figure 6:
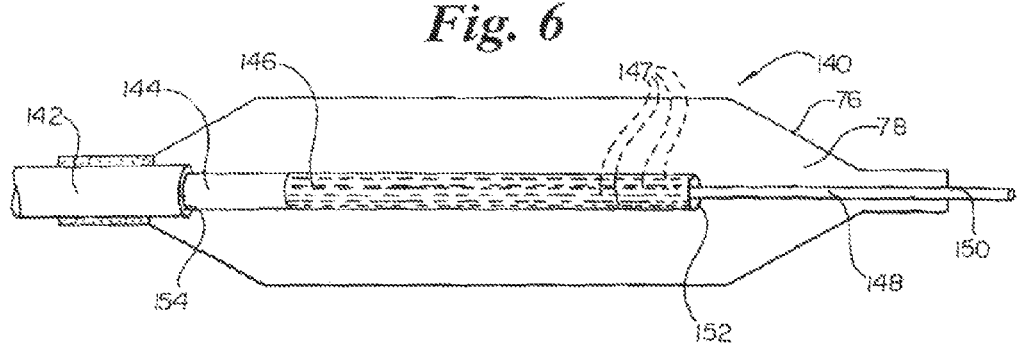
FIG. 6 is a fragmentary, cutaway, perspective view of a cooling catheter having a porous coolant distributor.

Referring now to FIG. 6, another cooling device 140 is illustrated, having generally a shaft 142 including a coolant supply tube 144 extending distally into a porous coolant distributor region 146 which can be formed as illustrated as a plurality of pores 147 extending through the tube walls. Cooling device 140 also includes a guide wire tube 148 having a guide wire lumen 150 extending therethrough. Porous region 146 has a distal end 152 which can be sealed tightly to guide wire tube 148 to prevent fluid from exiting through the porous region distal end. Device 140 can be used to deliver a liquid coolant which is delivered through the pores as a gas. the heat of vaporization being used to provide cooling. The gaseous coolant can serve to inflate balloon envelope 76, and, in the embodiment shown, exits balloon interior 78 through an annular exhaust or return lumen 154 which is disposed within shaft 142. In one embodiment delivering CO?, the exhaust lumen is terminated proximally by a pressure-regulating valve which serves to maintain the pressure of the balloon interior to at least the triple point of the CO2, to inhibit dry ice formation. In some embodiments, the coolant deliver}' pores are easily visible with the naked eye, having a nominal diameter of about 0.002 inches to 0.009 inches. In other embodiments, the pores are micropores, having a nominal diameter of about 10 microns to 50 microns. The pores distributed over the balloon length serve to distribute coolant over the length of the balloon interior. The coolant in the embodiment illustrated also serves to inflate the balloon against the vessel walls. In one application, cooling device 140 can be used to freeze tissue in a pulmonary artery or within the heart.

Referring now to FIG. 7, another embodiment of the invention is illustrated in a cooling device 160 having a proximal region 162 and a distal region 164. Device 160 includes a guide wire tube 166 extending through balloon 76 and terminating in an orifice 167. A coolant delivery tube 170 extends midway through balloon interior 78, having an annular coolant delivery lumen 178 therethrough, bounded by coolant delivery tube 170 and guide wire tube 166, Coolant delivery tube 170 is capped by a pressure relief type valve 172 which is urged proximally against coolant delivery tube 170 by a spring 168. Pressure relief valve 172 includes a proximal portion 180 adapted to sealingly fit over coolant supply tube 170 and a distal portion 182 dimensioned to slide over and seal against guide wire tube 166. Coolant device 160 can be used to cither inhibit restenosis through tissue cooling or to treat arrhythmias through tissue ablation with a pulmonary artery or within the heart.

Coolant is illustrated escaping from coolant delivery tube 170 at 174 into the balloon interior. Pressure relief valve 172 can be used in conjunction with a coolant undergoing a phase transformation from liquid to gas, such as liquid carbon dioxide. When the liquid coolant in the supply tube is warmed and attains a pressure exceeding the valve spring pressure, valve 172 slides distally, allowing the escape of coolant, typically in a gaseous form, into the balloon interior. Coolant can exit the balloon interior through a return or exhaust lumen 176, and can ultimately exit the proximal end of the catheter shaft. The exhaust lumen can be pressure regulated as well, to maintain a minimum pressure in the balloon interior.

Referring now to FIG. 8, another cooling device 190 is illustrated, having a distal region 192 and a proximal region 194. Cooling device 190 includes a coolant delivery tube 196 having a coolant delivery lumen 198 within and terminating in a distal coolant delivery orifice 200. Coolant can be supplied by a proximal coolant supply tube 212 in fluid communication with coolant lumen 198. A control handle assembly 214 includes a ring 208 biased proximally by a spring 210 and a control shaft 202 which extends distally through a seal 218 and lumen 198 to maintain the position of a valve 204 in tension against a valve seat 216. Control handle assembly 214 can be urged proximally to urge coupled valve 204 distally out of valve seat 216, allowing coolant to escape.

In use, distal orifice 200 can be disposed near a region to be cooled or cryoablated, followed by opening valve 204 and releasing coolant into the vessel region to be cooled or cryoablated. In some embodiments, valve control shaft 202 is a control wire incapable of providing substantial compression force, and the force to move valve 200 out of valve seat 204 is provided by the coolant pressure which can be provided through supply tube 212. In one embodiment, a liquid coolant is utilized which vaporizes to gas at the operating temperature and pressure, and the phase change urges valve 204 out of valve seat 206 when unconstrained by shaft 202 and ring 208, allowing escape of coolant as indicated at 206. Cooling device 190 can be used to deliver controlled doses of coolant at target sites without requiring an interposing balloon. Coolant can be distributed longitudinally over time by longitudinally moving delivery tube 196. In another embodiment, not requiring illustration, a spring is disposed against and supported proximally by a fixture to normally urge a valve seat distally against a valve seat. For example, spring 210 could be disposed distally of seal 218 and valve 204 could be disposed proximally of valve seat 216. In this embodiment, coolant can be released by retracting a control shaft proximally and moving a valve seat proximally from the valve seat. In this embodiment, a central shaft can be normally maintained in a state of compression which is released to open the distal valve and deliver coolant.

Referring now to FIGS. 9 and 10, a cooling device shaft region 230 is illustrated. Shaft region 230 can be located just proximal of a distal cooling portion such as a cooling balloon or coolant distributing portion. Beginning at the center, a guide wire 244 is disposed within a guide wire lumen 234 defined by a guide wire tube 232, A coolant supply lumen 236 is disposed about guide wire tube 232, defined by coolant supply tube 237, and is surrounded by a coolant return lumen 238, defined by a coolant return tube 239. One advantage of situating the coolant supply lumen centrally is situating the coolest fluid furthest away from the warmest fluid, the blood. A warming fluid return lumen 240 is disposed about coolant return tube 239, defined by a warming return tube 241, and a warming fluid supply lumen 242 can be disposed about warming fluid return lumen 240 and contained with a warming fluid supply tube 243. In a preferred embodiment, the warming jacket having the warming fluid supply and return lumens can provide warming to lessen unwanted cooling of the body vessel walls proximal of the target site. Cooling of a coronary artery region may be desired, or the cryoablating of a pulmonary artery or heart chamber region, but not the cooling or cryoablation of the vessel all the way from the point of entry to the coronary artery. As some heat transfer from the body to the coolant will occur proximal of the target site, the entering coolant will normally be cooler near the entry point of the catheter than near the target site. In many applications, excessively cooling the vessel walls may be undesirable. In particular, in some applications, while the distal region of the cooling device may be centered, the remainder of the device may be in direct contact with vessel walls.

To reduce the unwanted cooling, the warming fluid can provide a heat transfer layer between the coolant lumens and the vessel walls. In practice, the warming fluids may be of substantially less than body temperature, as the purpose is to reduce the cooling of the body vessel walls, not to warm the body vessel walls. The exact warming fluid temperatures and flow rates will depend on many factors and can be empirically determined by those skilled in the art. In some embodiments, the outermost tube wall material is formed of or coated with a less heat conductive material, to reduce heat transfer from the warm body walls into the coolant fluid.

Figure 11:
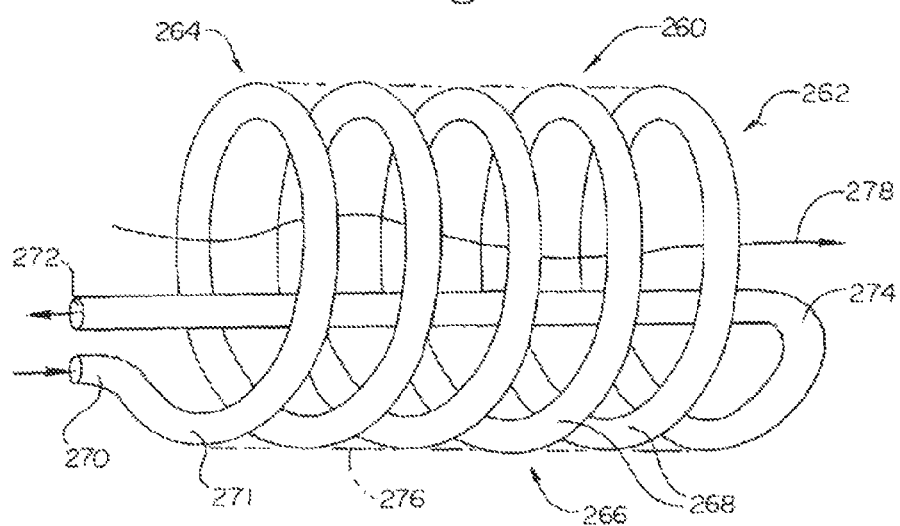
FIG. 11 is a fragmentary, perspective view of a cooling coil which can be used in a perfusion cooling catheter.

Referring now to FIG. 11, a subassembly perfusing cooling device 260 having a coil 266, a distal region 262 and a proximal region 264 is illustrated, which can be used in conjunction with other proximal catheter shafts and subassemblies well known to those skilled in the art. Coil subassembly 260 includes a coil inflow region 270 and a plurality of coil strands 268 formed in this embodiment from a single helical strand having a lumen 271 therethrough. Coolant can flow spirally and distally through the coil strands, returning through a centrally disposed return lube 274 and exiting the cooled region proximally at outflow region 272. The coil strands are preferably inflated with coolant under sufficient pressure to press the strands against the surrounding vessel walls, to provide good heat transfer from the walls to the coolant. In one embodiment, the coil 266 is enclosed in a jacket or envelope 276 which can aid in maintaining the coil shape integrity. The coil shape allows for long term cooling by allowing perfusing blood flow as indicated at 278. By allowing for perfusion, the vessel wall regions can be cooled for long continuous periods. In one method, a liquid coolant is used in conjunction with a coil such as coil 266. Coil 266 can be formed of materials such as Nitinol, stainless steel, polyimide, PET, or other balloon materials. Coil 266 may be particularly useful for circumferential cryoablation of a pulmonary artery region.

Figure 12:
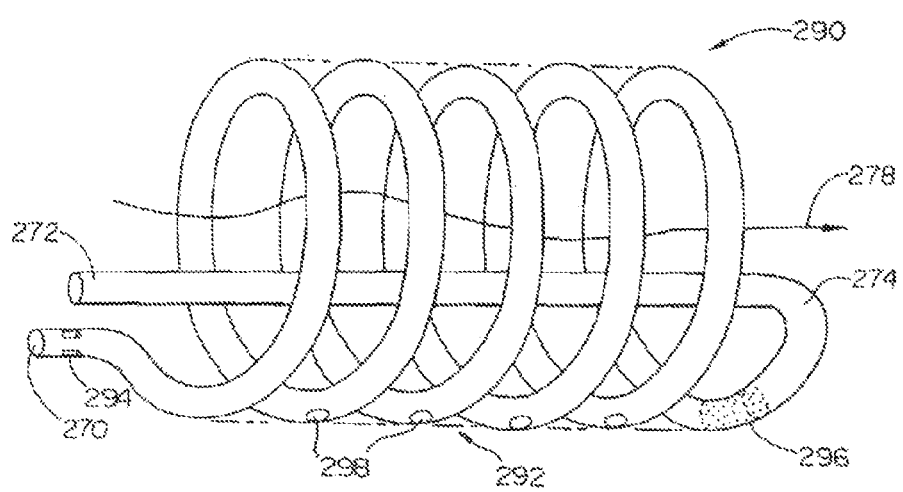
FIG. 12 is a fragmentary, perspective view of a coiling having an inflow pressure reducing orifice and an outflow fluid block which can be used in a perfusion cooling catheter having a liquid to gas phase change.

Referring now to FIG. 12, another cooling device subassembly 290 is illustrated, similar in many respects to cooling device subassembly 260 of FIG. 11. A cooling coil 292 includes inflow region 270 and centrally disposed outflow tube 274. Coil 292 includes a pressure-reducing orifice 270 in the proximal region of the coil and a fluid block or filter 296 in the distal region of the coil. Orifice 270 can provide a pressure drop and phase change from liquid to gas to provide enhanced cooling. Fluid block 296 can provide a trap to prevent fluid from entering return tube 274. Orifice 270 and fluid block 296 can provide an improved cooling coil for use with vaporizable coolants such as liquid carbon dioxide or Freon. The liquid can enter at 270 as a liquid and return at 272 as a gas. Coil 292 also includes a plurality of attachment points 298 for securing the coil to a longitudinal member. Cooling device subassembly 290 is believed particularly suitable for perfusion cooling of vessel walls using liquid coolants which are to undergo a phase transformation to cool the vessel region. Cooling subassembly 290 may also be particularly useful for circumferential cryoablation of pulmonary artery regions.

Figure 13:
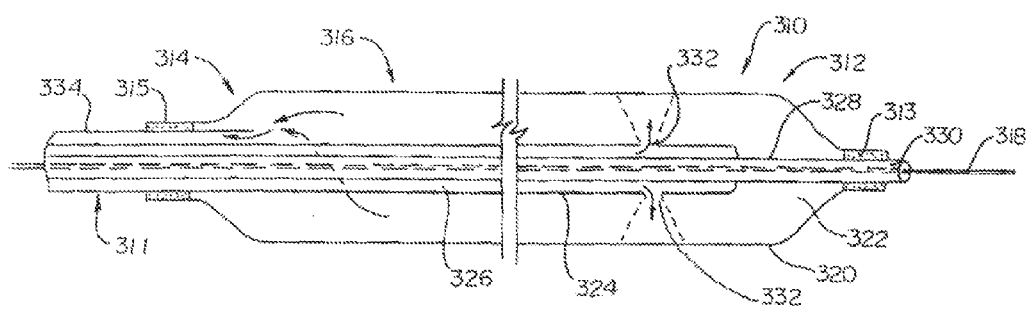
FIG. 13 is a fragmentary, longitudinal cross-sectional view of a coil, perfusion, cooling catheter in a straight configuration constrained by an inserted guide wire.

Referring now to FIG. 13, a cooling catheter 310 is illustrated, having a balloon 316 extending from a proximal region 314 to a distal region 312 and having a proximal end 315 and a distal end 313. Balloon 316 includes a balloon envelope 320 defining a balloon interior 322. Balloon 316 is disposed near the distal region of a catheter shaft 311 having a coolant delivery tube 324 defining a coolant delivery lumen 326 therein. Coolant delivery tube 324 can supply coolant to balloon interior 322 through coolant delivery orifices 332. A guide wire or stiffening wire tube 328 is disposed coaxially within coolant tube 324. Guide wire tube 328 includes a guide wire lumen 330 therein including a guide wire or stiffening wire 318 disposed within. Balloon envelope 320 can be bonded proximally to coolant tube 324 at 315 and bonded to guide wire tube 328 at 313. After entering balloon interior 322, coolant can flow proximally to a coolant return lumen 336 within a coolant return tube 334.

Cooling device 310 can be biased or preformed to assume a coiled shape when unconstrained. In FIG. 13, guide wire or stiffening element 318 extends through the balloon, constraining the balloon and preventing the balloon from fully assuming its coiled unconstrained shape. In some embodiments, a standard guide wire is used to maintain the constrained balloon shape. In other embodiments, a stiffening member having a distal region stiffer than the distal region of a standard guide wire is utilized. In a preferred embodiment, the balloon has a higher length to diameter ratio and a properly dimensioned balloon is not capable of occluding the vessel when inflated, as would an angioplasty balloon. In one embodiment, the device is biased to form a coil when unconstrained by forming coolant tube 324 and/or guide wire tube 328 of a material having a preformed shape which is reverted to when unconstrained. The distal tube sections can be formed of shape memory materials including shape memory polymers or metals, well known to those skilled in the art.

Figure 14:
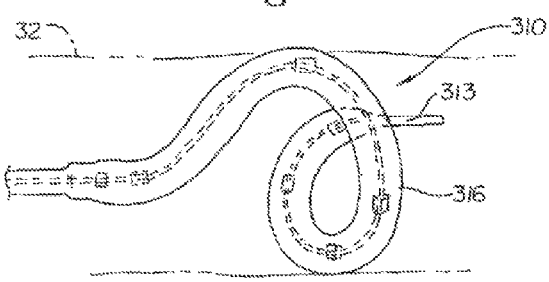
FIG. 14 is a fragmentary, perspective view of the cooling catheter of FIG. 13 is an unconstrained, coiled configuration within a vessel.

Upon retraction of guide wire 318, balloon 316 can assume the coil shape illustrated in FIG. 14. In the embodiments of FIG. 14, balloon 316 forms a single coil capable of cooling or cryoablating a short region of vessel 32. Device 310 can be used to cool vessel wall regions while allowing for perfusing blood flow through the coil center. In other embodiments, multiple coils are formed, allowing for the cooling of longer vessel wall regions. In use, device 310 can be advanced over a guide wire to a site to be cooled. Once in position near a region that has been dilated or is to be dilated, guide wire 318 can be retracted, allowing the balloon to form a coil. Either before or after the coil formation, coolant can be injected into the coolant lumen, allowing coolant to enter balloon interior 322. With the balloon disposed near or against the vessel walls, the vessel walls can be cooled or cryoablated while allowing perfusing blood to flow through the coil center. After sufficient cooling has occurred, coolant inflow can be stopped, and guide wire 318 can be re-inserted through guide wire lumen 330, imparting a straighter shape to the balloon. Cooling device 310 can be retracted from the blood vessel in the straighter configuration.

Figure 15:
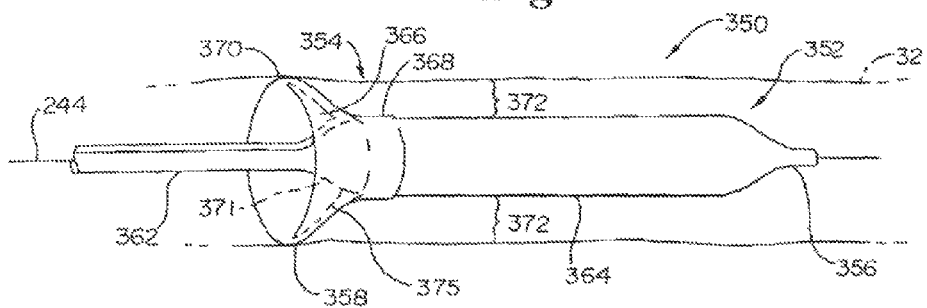
FIG. 15 is a fragmentary, perspective view of an occluding cooling balloon catheter disposed in a vessel and smaller in profile than the vessel region being cooled.

Referring now to FIG. 15, another cooling device 350 is disposed within blood vessel 32. In some embodiments, device 350 is similar in many aspects to cooling devices having balloons previously discussed. Cooling device 350 is dimensioned to allow cooling of the vessel wall without requiring the cooling balloon to directly contact the vessel wall. Device 350 has a distal region 352, a proximal region 354, and a distal tip 356. A cooling balloon 364 is illustrated and can be similar to cooling balloons previously discussed with respect to other embodiments. Balloon 364 has an outer diameter selected to be less than the inside diameter of vessel 32 in which it is disposed. A proximally disposed occluding device 358 including an expandable outer rim 370 is secured to balloon 364 through a proximal skirt 366 at a proximal waist 368. A shaft 362 including guide wire 244 within is illustrated extending proximally of proximal occluding device 358. Shaft 362 can be similar to shafts previously discussed and can vary with the type of balloon used in the device. Shaft 362 can include lumens for coolant supply and return and lumens for inflation fluid.

By dimensioning the balloon to have a profile less than the vessel cross section, an annular space 372 remains between balloon 364 and vessel 32. The annular space can contain a relatively quiescent blood volume due to the occluding effect of occluding device 358. Occluding device 358 contacting vessel 32 can block most blood flow past the balloon, leaving an unchanging volume of blood. The cooling provided by balloon 364 can cool this still volume of blood, cooling the blood and thereby cooling the vessel walls adjacent to the blood. Cooling device 350 can thus cool the vessel walls and any stenosis without contacting the vessel walls which can be advantageous where there is a desire to avoid contacting the vessel walls directly.

Occluding device 358 can be formed of any suitable expandable device, preferably a reversibly expandable device. In one embodiment, expandable outer rim 370 includes an inflatable outer tubular portion 371 and an inflatable double-walled envelope skirt portion 375 in fluid communication with the interior of balloon 364, such that inflating balloon 364 inflates proximal skirt 366 and outer rim 370 to expand against the vessel walls. In one embodiment, the skirt is not itself inflatable but includes tubular lumen portions for inflating the outer rim. After cooling is complete, in one embodiment, the coolant which serves as the inflation fluid is withdrawn and the proximal skirt contracts to a smaller profile configuration. In some methods, a vacuum is pulled on the lumen in fluid communication with the proximal skirt. In another embodiment, after cooling is complete, both coolant and a separate inflation fluid are withdrawn followed by pulling a vacuum on the inflation lumen, thereby contracting the proximal skirt even further.

In use, cooling devices according to the present invention can be used to cool an area having a lesion and/or in close proximity to an area having a lesion, where contact with an angioplasty balloon or other vessel dilating device is expected. The cooling devices can be used to cool a vessel area where possible irritation or injury is possible during a medical procedure. For example, cooling can be performed in an area where atherectomy or ablation is to be performed. The cooling can also be used to lessen any adverse impact of minimally invasive surgical procedures including cardiac artery bypass surgery. The cooling can be performed either before or after the medical procedure or both before and after the procedure. The cooling is believed by Applicants to lessen the post-procedure injury response which can include restenosis in the case of angioplasty.

The vessel walls are preferably cooled for a temperature and period sufficient to encourage a positive remodeling response after the medical procedure. The cooling is preferably for a temperature and time not so severe as to irreversibly harm the vessel walls. In particular, freezing the vessel walls to the point of causing necrosis is preferably avoided. In one method, the vessel walls are cooled to a temperature of between about 0 degrees C. and about 10 degrees C. for a period of between about 1 minute and 15 minutes. In a preferred method, the vessel walls are cooled for a period of between about 5 minutes and 10 minutes. In one method, the vessel walls are cooled for a period of about 10 minutes between about 0 and 10 degrees C. In some methods, cooling is limited in time to the time for which occluding the vessel is permitted. In some methods, cooling periods are alternated with blood flow periods. In some methods utilizing perfusion cooling devices, cooling can be performed for longer periods because blood flow is allowed during the cooling process.

In use, cooling devices according to the present invention can also be used to cool an area to the point of freezing tissue, for the purpose of ablating tissue to treat arrhythmias. Sites for such treatments include the inner walls of the heart chambers and the inner wall of a pulmonary vein.

In some methods, ultra sound is used to monitor the freezing of tissue near the cooling device. Frozen tissue is more transparent to ultrasound than unfrozen tissue, making frozen tissue show up differently than the surrounding unfrozen tissue. Monitoring the cooling with ultrasound can provide an indication of when the cooling process has proceeded too far. Applicants believe the freezing of water in cells can be visualized before irreversible damage and cell death has been caused. In most methods, fluoroscopy is used to monitor the position of the cooling device relative to the lesion to properly position the cooling device distal region. In one method, the temperature of the balloon wall is measured with an external temperature probe such as a thin film, device. The temperature of the vessel wall can also be estimated by measuring the balloon wall temperature, either from the inside or outside of the balloon envelope wall. The temperature of the incoming and outgoing coolant is measured in some embodiments.

In a preferred method, the pressure inside the cooling device and/or inflatable balloon is measured. Measuring the coolant pressure is particularly desirable in embodiments where the coolant undergoes a liquid to gas phase change inside of the device. In one method, carbon dioxide is used as a coolant and the pressure of the gaseous coolant is monitored to insure the pressure does not become so high as to stress the device, and to insure the pressure does not become so low as to allow dry ice formation. Embodiments utilizing liquid carbon dioxide and having a return lumen for the gaseous carbon dioxide preferably maintain the gas pressure above the triple point of carbon dioxide so as to inhibit dry ice formation within the cooling device. Some devices utilize a high-pressure liquid to low-pressure liquid drop across a pressure reducing device such as an orifice. The pressure of the inflow and outflow coolant can be used to monitor the cooling process in these devices as well.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A treatment catheter, comprising:
    a treatment assembly having a central axis, a distal portion and a proximal portion axially spaced along the central axis, the treatment assembly including a plurality of treatment regions and a shapeable region moveable between a delivery shape and a deployed shape, wherein the plurality of treatment regions are carried by the shapeable region, wherein the treatment assembly has a substantially linear shape in the delivery shape and a helical shape in the deployed shape; and
    a control member operably coupled to at least a portion of the treatment assembly and disposed along the central axis, wherein movement of the control member relative to the distal portion of the treatment assembly moves the treatment assembly between the delivery shape and the deployed shape.

2. The catheter of claim 1, wherein the treatment assembly assumes the helical shape when unconstrained.

3. The catheter of claim 1, wherein the helical shape includes a plurality of helical coils.

4. The catheter of claim 1, wherein proximal movement of the control member relative to the distal portion of the treatment assembly places the treatment assembly in the deployed shape and distal movement of the control member relative to the treatment assembly places the treatment assembly in the delivery shape.

5. The catheter of claim 1, wherein the treatment assembly defines a lumen and the control member is a guidewire configured to extend through the lumen.

6. The catheter of claim 5, wherein the treatment assembly includes an expandable balloon.

7. The catheter of claim 6, wherein the balloon includes a coolant lumen.

8. The catheter of claim 7, wherein the coolant lumen includes one or more spaced apart coolant delivery orifices.

9. The catheter of claim 7, wherein the balloon is configured to be inflated with cooling fluid.

10. The catheter of claim 7, wherein the balloon is configured to be inflated with inflation fluid that differs from cooling fluid.

* * * * *